United States Patent [19]
Schindler et al.

[11] Patent Number: 5,477,855
[45] Date of Patent: Dec. 26, 1995

[54] SHIELD FOR CONDUCTORS OF AN IMPLANTABLE DEVICE

[75] Inventors: Robert A. Schindler, Hillsborough; Charles L. Byers, Santa Clarita; Alfred E. Mann, Beverly Hills; James W. Beazell, Rancho Palos Verdes, all of Calif.

[73] Assignee: Alfred E. Mann Foundation for Scientific Research, Sylmar, Calif.

[21] Appl. No.: 92,748

[22] Filed: Jul. 16, 1993

[51] Int. Cl.⁶ ............................................. A61B 5/04
[52] U.S. Cl. ............................................. 128/642; 607/37
[58] Field of Search .................................. 128/642, 673, 128/634, 635, 736, 908; 607/36, 37, 38, 113, 116, 51, 117, 118, 130, 129, 131; 606/129, 117

[56] References Cited

U.S. PATENT DOCUMENTS 5,143,089  9/1992  Alt ................................... 128/642

Primary Examiner—Lee S. Cohen
Assistant Examiner—Brian M. Green
Attorney, Agent, or Firm—L. Lee Humphries

[57] ABSTRACT

A shield for the conductors extending from an implantable device, provides a cover for the conductors and protects them against being dislodged or moved, by scratching, physical activity, skin pressure or other circumstance. The cover is resilient and flexible and is made of a fabric laminated between layers of an elastomer, such as silicone rubber. The cover is fixedly attached at one end with respect to the implantable device. The cover is suturable to hold the implantable device, cover and conductors in place, thereby providing stabilization. The shield is disposed over the location where the conductors extend from the implanted device and provides strain relief for the conductors and protects them from breakage at that very fragile location. The shield partially or totally encircles the conductors for a short distance.

31 Claims, 4 Drawing Sheets

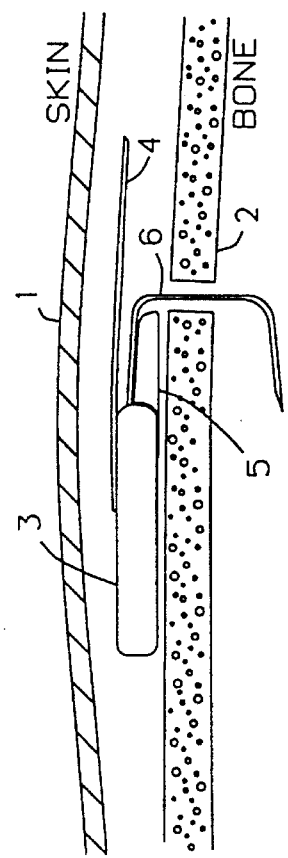
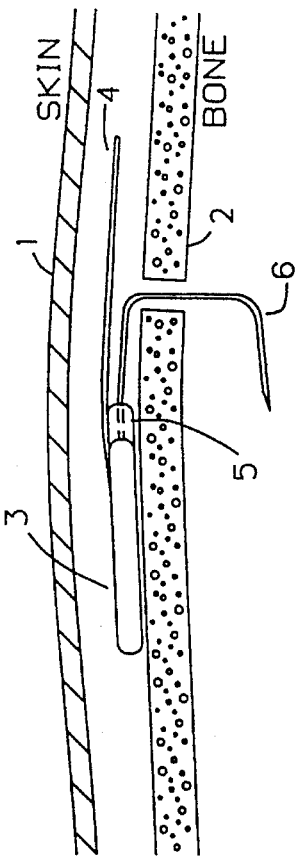
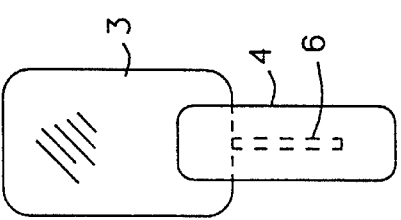
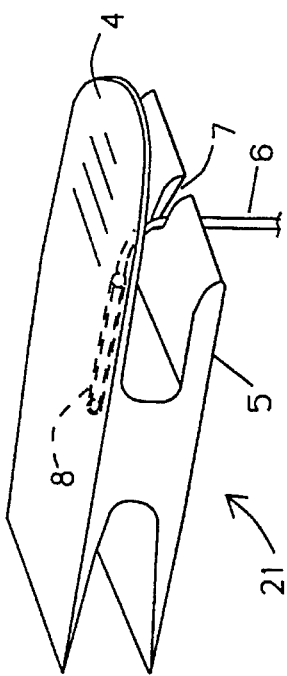

SHIELD FOR CONDUCTORS OF AN IMPLANTABLE DEVICE

This invention is a protective shield for the protection of the conductors of an implantable device. The shield attaches to the implantable device and extends over the conductors, to protect them against being dislodged, moved or otherwise affected by scratching, physical activity, skin pressure or other circumstance.

Three purposes are accomplished by the shield, protective cover, strain relief of the conductors and the stabilizing of the conductors and the implanted device.

Implanted devices commonly have electrical conductors emerging from them or extending from them. Also, a particular implanted device might have other kinds of conductors such as, without limitation, optical fibers, hydraulic tubes, acoustic tubes or fluid tubes. The device of the invention provides cover protection, strain relief and stabilization for all types conductors.

A particular advantage provided by the shield of the invention is that it allows conductors to be designed to be much smaller because of the protection they receive. Formerly, conductors had to be ruggedly constructed and, therefore, had to be larger, so as to avoid being broken or over-stressed. Also, a larger hole was required where the conductor passed through bone or tissue. The use of much smaller conductors are an advantage provided by the device of the invention.

The shield comprises a cover which first provides a protective shield for one or more conductors in order to minimize moving or dislodging of the conductor. Sometimes, a patient will scratch or bump the area of an implant, which may cause the conductors of the implant to be moved or dislodged. The device of the invention provides a barrier against the conductors being affected by such scratching, bumping or other contact with the skin.

Secondly, the conductors are protected against strain, by the device of the invention. This is particularly important at the location the conductors extend from the implanted or implantable device. A sharp bend or strain, or any transverse pressure at or near the point where the conductors emerge from or connect to the case of the implanted device, could cause the conductor to break or be damaged. Some implantable electrical conductors are as small as 0.001 of an inch in diameter and are, therefore, quite fragile. The shield of the invention provides strain relief for the conductors at the location where they extend from the implantable device and for a distance along the lengths of the conductors by partially or entirely encircling such conductors.

The shield thirdly serves to stabilize the conductors and the implanted device against motion within the patient's body. In a preferred embodiment and use, the shield, which is adhered or otherwise affixed to the implanted device, is sutured to the skin, muscle or tissue of the body.

It, therefore, is an object of this invention to provide a cover for the conductor or conductors of an implantable device.

It is also an object of this invention to provide a shield which provides strain relief for the conductors of an implantable device.

It is another object of this invention to provide a stabilizing shield for the conductors of an implantable device.

Another object of this invention is to provide a supportive shield for the conductors of an implantable device.

A further object is to provide a shield encircling the conductors of an implantable device.

Still another object of the invention is to provide protection for the conductor end of an implantable device.

Further objects and features may be seen from the drawings and description which follows.

FIG. 1 is a cross-section of the skin and bone of a patient, showing the side view of an implanted device having a shield comprising a cover and a bottom shield.

FIG. 2 is a top view of an implantable device, showing a shield comprising a cover only.

FIG. 3 is a cross-section of skin and bone of a patient, showing an implantable device having a shield comprised of a cover and bottom shield which fit over the end of the implantable device.

FIG. 4 is a perspective of a shield comprising a cover, a bottom shield having a slot, and in which the cover and the shield comprise a unitary structure including a channel disposed between the cover and the bottom shield.

FIG. 6 is an illustration of a shield comprised of a cover and bottom shield constructed as two pieces, and the bottom shield having a closed slot for the conductor or conductors to readily pass through.

FIG. 7 is an illustration of a shield having a cover and a bottom shield comprising a single structure and in which the bottom shield has an open slot for the conductor to pass through.

DETAILED DESCRIPTION

Figure 5:
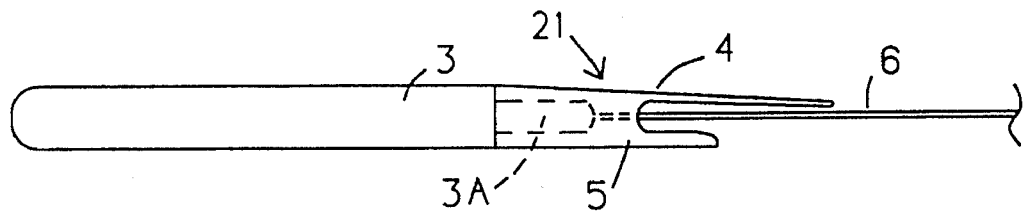
FIG. 5 is a side view of a shield comprised of a unitary structure, fitted over the end of an implantable device.

In FIG. 1 is shown a cross-section of skin 1 and bone 2 of a patient, showing a side view of an implanted device 3 having a shield comprising a cover 4 and a bottom shield 5, which are fixedly mounted with respect to implantable device 3. Cover 4 is shown as being flat. Preferably, it is flat or planar but it may be curved. Conductor 6 extends from the case of implanted device 3 and, in the case shown, extends through the bone 2, or tissue, into some other area of the patient's body. The implanted device 3 may be implantable between the skin and bone, the skin and muscle, or other tissue. The device of the invention is not limited to implants between the skin and underlying bone, as shown in FIG. 1. Also, the shield finds wide use wherein the conductor 6 extends longitudinally from the implanted device 3. Because of the congruous construction of the shield with the implanted device 3, the shield is readily applied to implantable devices which are implanted just under the skin, on the skull or other bones of the head. However, its usefulness extends to other implantable devices which are planted deeper, such as those planted next to, and, even, underneath a muscle, organ or other body tissue.

In FIG. 1, conductor 6, or conductors, are protected from external skin pressure, which is absorbed or deflected by cover 4, which extends in cantilevered fashion from implantable device 3. If a patient scratches his skin, he scratches the skin against the cover and not against a conductor. If the cover 4 is pressed against the conductor, no damage is done, because the cover takes the effect of the scratching and distributes any localized pressure or pressure transmitted through the body of the patient. If a person is bumped in the area of the conductor, the conductor is less likely to be affected, having cover 4 protecting it.

It is to be appreciated that, although a single conductor 6 is shown, such conductor may contain several conductors. Further, the conductor 6 is typical and representative of any number of conductors emerging separately from implantable device 3.

In the device of the invention, the cover 4 and bottom shield 5 are preferably made of woven, (tightly woven or otherwise), biocompatible fabric such as, without limitation, a polyester, disposed between laminations of a biocompatible elastomer. Such polyester and elastomer layers may be molded and die cut. A particularly preferred polyester fabric is Dacron and a preferred elastomer would be silicone rubber or Silastic. Other polymers, which may not necessarily be biocompatible, may be used for the fabric provided they are enclosed within laminations of the elastomer and are stable therein. Some epoxies may be used but ordinarily they would tend to be too stiff and tend to break up over periods of time, when implanted within the body. Other implantable elastomers are readily available from firms such as Dow Chemical of Midland, Mich., and E. I. DuPont DeNemours and Co. of Wilmington, Del. It is desired that the cover 4 be smooth and that the skin or nearby tissue slide smoothly on it. The cover 4 is laminated preferably and composed of two or more layers. For example, cover 4 may be constructed by disposing a woven layer of fabric, such as a polyester fabric, between layers of an elastomer. Such fabric provides reinforcement to the elastomer cover so that it may be sutured to the bone, muscle, skin, or as otherwise may be desired. The polyester fabric, disposed within an elastomer, such as silicon rubber, will hold the suture for an extended period of time, that is, for several months and even several years, without separating. Otherwise, without the fabric, the suture is likely to eventually cut through and separate from a cover made entirely of an elastomer. The suture, of course, must be of a material that does not dissolve too quickly in the body, but must be a material that lasts for as long as the implanted device must remain in place. Suturing threads made of various polymers are available for long-lasting sutures. Suturing the protective shield to the patient, stabilizes the shield, the implanted device 3 and the conductor 6 as well, in the implanted location.

If it is not intended to suture the cover, the woven material may be eliminated and a single layer of silicone rubber or other suitable elastomer may be used. The cover 4 is designed to be compliant. However, it may be constructed with some stiffness at its fixed end to provide protection for the conductor 6, or conductors, at the location conductor 6 extends from the implantable device 3. Stiffness of the shield, particularly close to the implanted device 3, is for the purpose of preventing the extreme, or sharp, bending, or transverse motion, of the conductor 6, particularly as it extends or emerges from the implanted device 3. A sharp bend could easily break the conductor 6, or the structure feeding the conductor 6 through the case of the implanted device 3. In one embodiment, the cover 4 may have sufficient stiffness and resilience to spring at least partly away from the conductors, at the location near the implanted device 3, if pressed against such conductors.

The cover 4, in FIG. 1, may have a thickness of 3 to 100 thousandths of an inch. Twenty to forty thousandths of an inch is an optimum range, if the cover 4 is made of silicone rubber or other elastomer. Forty thousandths works very well. Such structure provides a resilience, giving the desired protection to conductors such as conductor 6. Of course, other thicknesses and lengths may be desirable under various circumstances. In some instances, a stiffer shield may be desired, but, ordinarily, a resilient, compliant shield is preferable, so as to be flexible under the skin, unnoticeable and not cause irritation. A preferred embodiment is thus one in which the cover 4 is more flexible than the bottom shield 5.

FIG. 2 is a top view of the implantable device 3, showing a shield comprised of a planar, cover 4 only. In this embodiment, no bottom shield is included. Conductor 6 is shielded and covered by cover 4 which extends beyond the length of conductor 6. If conductor 6 turns in a different direction away from the cover 4, as shown in FIG. 1, cover 4 extends at least as far as the turn and, preferably, somewhat farther to provide adequate protection and cover to conductor 6.

The device of FIG. 2 illustrates that cover 4 is wider than the conductor 6, but may not be as wide as the implantable device 3. In other instances, cover 4 may be constructed as wide as, or wider than, implantable device 3. Cover 4, even when used alone, aids in stabilizing the position of the implantable device, within the patient's body, as well as stabilizing the position of the conductor or conductors. It may be sutured if desired, in order to provide better stabilization of the implanted device and the conductors.

Cover 4, in FIG. 2, is affixed or adhered by medical grade adhesive, epoxy or other suitable means, to the case of implantable device 3. Med A is a suitable silicon adhesive available from Dow Chemical of Midlands Mich. Implanted device 3 may be specially constructed or designed to receive and retain cover 4.

FIG. 3 is another cross-section of skin 1 and bone 2 of a patient, showing, in side view, an implantable device 3 having a shield comprised of a cover 4 and bottom shield 5 which fit over the end of the implantable device 3. Bottom shield 5 is shorter than cover 4 and may be made wider or narrower than cover 4, as desired.

It may be noted that this embodiment provides substantially better strain relief for the conductor 6 at the point it emerges from the implantable device 3. Sharp bending and transverse movement of conductor 6, at its location of emergence from the implantable device 3, is prevented. Thus, strain relief is provided by the shield. Further, conductor 6 is better enclosed and protected at the location it extends or emerges from implantable device 3.

Further, by enclosing at least a portion of the conductor 6, right at the point of where it extends from implanted device 3, and further isolating conductor 6, tissue is prevented from filling in around the conductor 6, right at the implanted device 3. If tissue fills in the area around the conductor 6, external skin pressure and internal muscle pressure may be undesirably transmitted to the conductor 6. The structure of FIG. 3 is designed to prevent such undesirable growth near the location the conductor 6 extends from or emerges from implanted device 3.

It is also noted that cover 4, by its size and shape, provides for anchoring, or stabilizing, the implanted device 3 and conductor 6 within the patient's body. Anchoring and stabilizing may be further achieved by suturing cover 4 to the skin, tissue or other body part.

FIG. 4 is a perspective of a shield 21 comprising a cover 4 and the bottom shield 5. Cover 4 and bottom shield 5 may be cast, molded or otherwise constructed in two or more parts or as a unitary structure. However manufactured, it is preferably combined, prior to implanting, into a unitary structure by an adhesive or other means of integrating cover 4 and bottom shield 5 into a single article. A channel 8 is disposed between the cover 4 and bottom shield 5, or through bottom shield 5, allowing the conductor, or conductors, to pass through the shield 21. Bottom shield 5 may have a slot, such as slot 7, through which conductor 6 may readily pass. The bottom shield 5 should extend at least a short distance from the implantable device. The distance would be determined by how far it is desired to support or stabilize the conductors emerging from the implantable device 3. The bottom shield 5 should extend far enough so that if the conductor 6 is bent, little or no torsion or other stress is conveyed to the fragile point where the conductor extends from the implantable device. The location where the conductor emerges, or is connected to, the implantable device, is where substantial danger of conductor breakage exists.

The device of FIG. 4 is approximately the same width as the implantable device to which it is attached.

The device of FIG. 4 and other embodiments described herein, stabilize the conductors against bending and against transverse motion relative to the implanted device. By transverse motion is meant motion in the shear direction or transverse to the longitudinal direction of the conductors. Such bending or transverse motion would be particularly hazardous to the conductors at their point of connection to or emergence from the implanted device.

It is also pointed out that tissue growth is prevented around conductor 6 close to the implanted device 3 by reason of conductor 6 being enclosed in channel 8.

The shield 21 of FIG. 4 may be readily cast of inert, biologically-compatible elastomer having some resilience. Alternatively, it may be constructed in two parts, in which cover 4 may be die-cut and adhered or affixed in some manner to bottom shield 5. Various biomedical grade fabrics or fabric-like material, may be found suitable to be laminated within cover 4, but a polyester such as Dacron appears to be the most suitable. In constructing the cover 4 and the bottom shield 5, various epoxies and acrylics may also be used, or combinations of various plastic-impregnated woven material provided they have sufficient stiffness for bottom shield 5 and sufficient resilience for cover 4. They must be biologically suitable for implantation and be able to withstand the intended environment and usage. The shield 21 may be cast, or otherwise constructed, to fit the implantable device so as to be readily attached thereto.

Adhesives, clamps, fasteners, sutures or other known methods of firmly attaching the shield 21 to the implantable device 3 may be used. The simplest and easiest method of attachment, of course, is by the use of an adhesive.

FIG. 5 is a side view of a shield 21 comprised of a unitary structure, fitted over the end of the implantable device 3, which has an extension 3A. Shield 21 is adapted to receive extension 3A. The cover 4 is shown as being slightly longer than the bottom shield 5. The cover 4 extends longitudinally for a distance along the conductor which, in this example, continues on, in generally the same direction.

Figure 6:
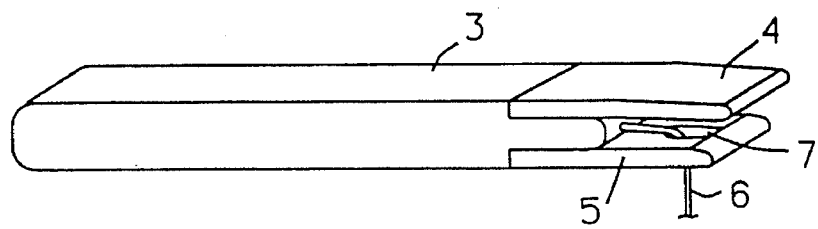

FIG. 6 is an illustration of the cover 4 and the bottom shield 5 constructed as two pieces, which fit into recesses provided by the implantable device 3. Bottom shield 5 is shown as having a slot 7 for conductor 6, or a plurality of conductors, to readily pass through. It is noted that slot 7 is closed in this embodiment and the conductor 6 or a plurality of conductors are threaded through slot 7. In this embodiment, the closed slot 7 provides greater constraint against movement by the conductors and holds them in place better than does an open slot.

Figure 7:
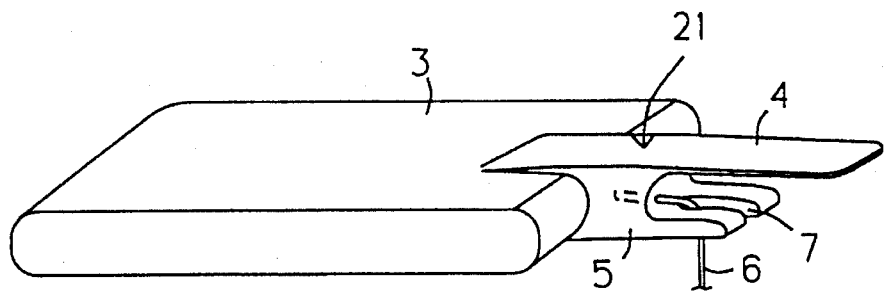

FIG. 7 is an illustration of a protective shield 21 having a cover 4 and a bottom shield 5 constructed as one piece, or as a unitary structure. Bottom shield 5 has an open slot 7 for the conductor 6, or a plurality of conductors, to pass through.

It is noted that in the construction of FIG. 7, cover 4, even if quite resilient, would not touch or would barely touch conductor 6, if depressed close to implantable device 3. The spacing of cover 4, together with the stiffness of the material of which it is composed, prevents any substantial bending of cover 4 near the implanted device 3 where conductor 6 emerges. Thus, conductor 6 is protected from strain or bending at its most fragile location, that is, where it either emerges or extends from implanted device 3.

Figure 8:
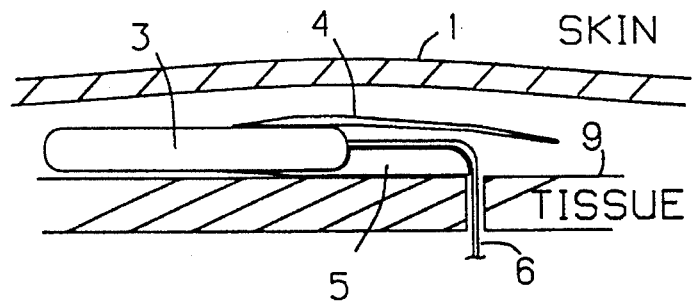
FIG. 8 is a side view of a shield having a cover and a bottom shield, adapted to rest on somewhat firm structure of the patient's body and the conductors rest on the bottom shield, at least at one or more locations.

FIG. 8 is a side view of a protective shield having a cover 4 and a bottom shield 5 which rests on somewhat firm tissue 9, bone or other structure of the patient's body, and the conductor 6 rests on the bottom shield 5, at least at one or more locations. Bottom shield 5 may have a groove, or multiple grooves therein, to accommodate conductor 6 or a multiplicity of conductors, to hold such conductor or conductors in place. The electrical conductors may even be adhered in place in such grooves.

Figure 9:
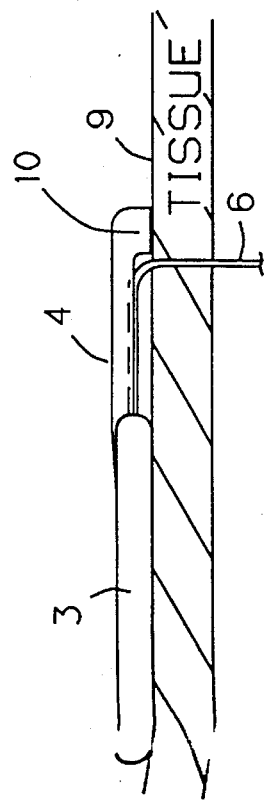
FIG. 9 is a side view of a shield which partially encompasses the conductors by reason of the cover being L-shaped in profile.

FIG. 9 is a side view of a protective shield which partially encompasses the conductor 6, or a plurality of conductors, by reason of the cover 4 being L-shaped in profile. There is no bottom shield in the preferred embodiment of FIG. 9 although one could be so constructed. The end 10 of cover 4 may rest on tissue or other firm structure or may simply resiliently extend in cantilever fashion from implanted device 3. The cover is long enough to encompass the bend portion of conductor 6. Conductor 6 may be adhered to cover 4.

Figure 10:
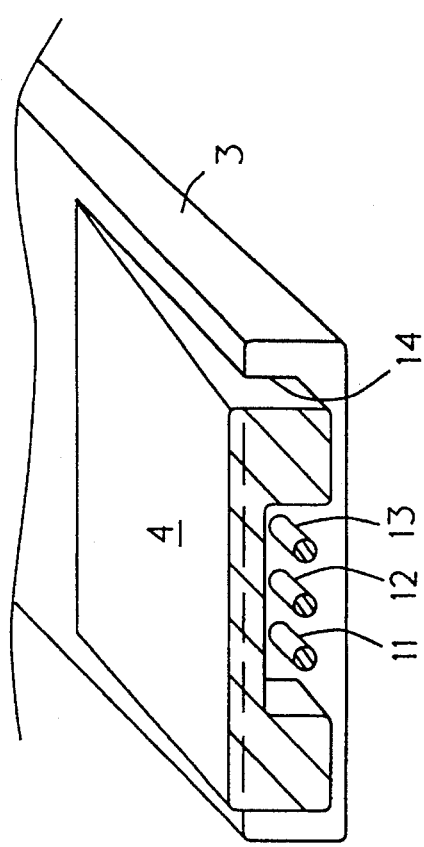
FIG. 10 is an illustration of the cover in cross-section taken a short distance from the end of the implantable device, showing the emerging conductors, also in cross-section, and the cover being channel-shaped, and, thus, partially encircling the conductors.

FIG. 10 is an illustration of another embodiment of the cover 4 in cross-section a short distance from the end of the implantable device 3, showing the emerging conductors 11, 12 and 13, also in cross-section. In this embodiment, the cover 4 is channel-shaped, and, thus, partially encircles the conductors 11, 12 and 13. Additional stiffness of the cantilevered cover 4, at the emergence of the conductors 11, 12 and 13 from implanted device 3, is obtained by it having an abutment against the end of the implanted device 3, as shown at location 14.

Figure 11A:
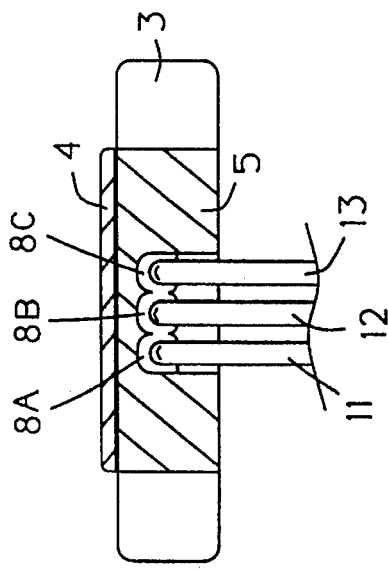
FIG. 11A is a cross-section taken on line 11A—11A of FIG. 11, showing more clearly the channel 8.
Figure 11:
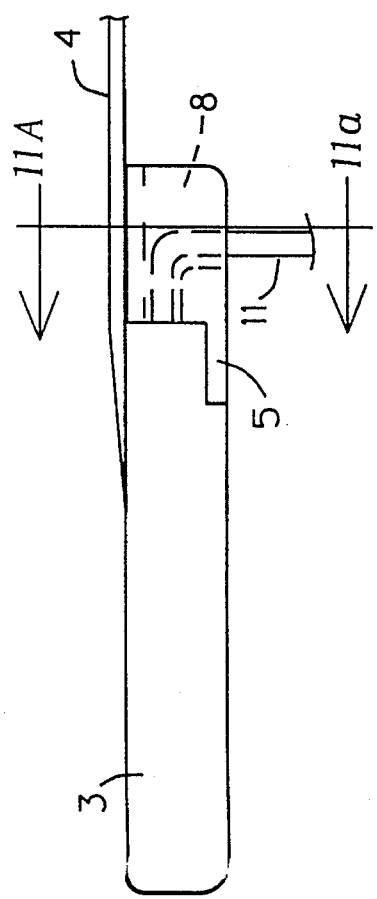
FIG. 11 is a side view of a cover and a bottom shield having a channel therethrough.

FIG. 11 is an illustration of a cover 4 and a bottom shield 5 having a channel 8 therethrough. The cover 4 extends along implantable device 11 and may be adhered to either it or the bottom shield 5 or both.

FIG. 11A is an cross-section taken on line 11A—11A of FIG. 11, showing more clearly the channel 8. FIG. 11A shows implantable device 3, cover 4 and a bottom shield 5 with a channel 8, comprised of three bores 8A, 8B, and 8C, through which the conductors 11, 12 and 13 pass. FIG. 11A shows how cover 4 is spaced apart from conductors 11, 12 and 13. FIG. 11A illustrates how a plurality of conductors may be accommodated and how they might be better constrained within bores 8A, 8B, and 8C, which form a single channel 8.

Figure 12A:
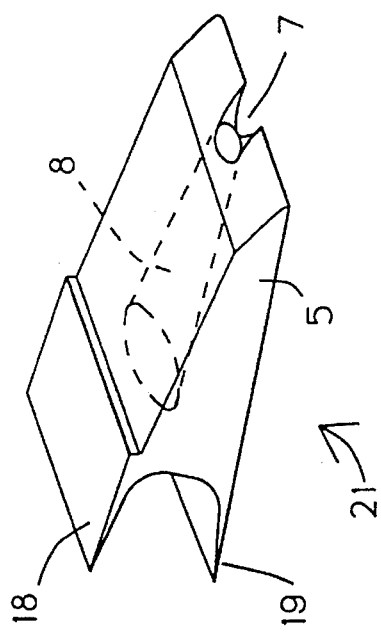
FIG. 12A is the embodiment of FIG. 12, with the cover removed.
Figure 12:
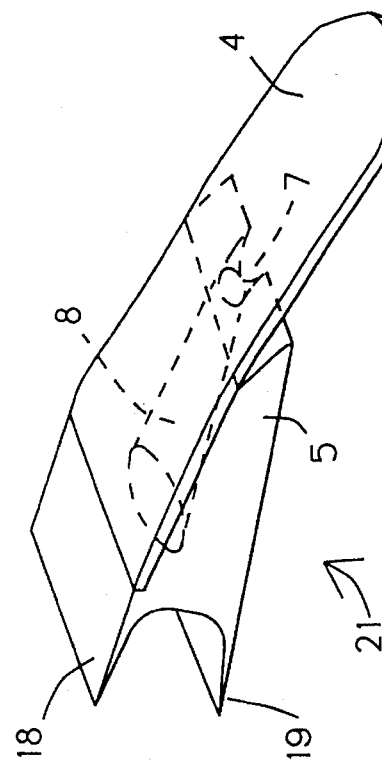
FIG. 12 is a perspective of a preferred embodiment of the shield which encircles the conductors emerging from the implantable device and in which the cover extends in cantilever fashion from the bottom shield.

FIG. 12 is a perspective of the preferred embodiment of the shield 21 in which the cover 4 extends from a shelf on bottom shield 5 which entirely encircles the conductors emerging from, or connected to, the implantable device. Channel 8 provides a conduit for the conductors of the implantable device to pass through, and continue within the patient's body. Channel 8 is shown as converging. It is desirable that channel 8 converges to a close fit with the conductors passing through it, so as to provide restraint and to avoid the conductors being flexed, stressed, bent or moved transversely near the point of their extending from implanted device 3, where they are most fragile. Channel 8 opens downwardly into slot 7 and thus allows the conductor or conductors to bend downwardly, away from cover 4. Cover 4 may be adhered to bottom shield 5 by Med A or other medically and chemically-suitable adhesive and in this way, the shield 21 is constructed to be a unitary structure. In this preferred embodiment, cover 4 is comprised of Dacron fabric contained between two layers of silicone rubber.

Lips 18 and 19 are adapted to receive the implantable device and be adhered or otherwise affixed thereto. Lips 18 and 19 are faired, or tapered, to very thin edges, to avoid a noticeable ridge along their edges, when adhered to the implantable device.

It is noted that cover 4, at its distal end, the far end from the implantable device, is resiliently movable with respect to the conductor, the bottom shield 5 and the implantable device.

FIG. 12A is the embodiment of FIG. 12, with the cover 4 removed. It may readily be seen how channel 8 converges to closely fit any conductors which it may carry. By comparing FIGS. 12 and 12A, it may be seen how cover 4 fits onto bottom shield 5 and may be adhesively fixed thereto.

Figure 13:
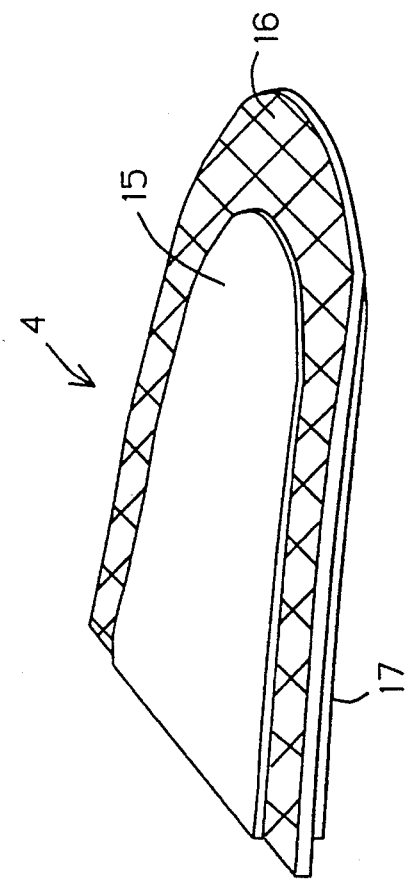
FIG. 13 is a further detail of one embodiment of the cover shown in FIG. 12.

FIG. 13 is a further detail of one embodiment of the cover 4. Cover 4 is comprised, in this embodiment, of three laminated layers, as described in connection with FIG. 12. Layer 15 of silicone rubber, or other elastomer, lies on a fabric preferably Dacron, which, in turn, lies on layer 17 made of silicone rubber. In the embodiment of FIG. 13, however, the Dacron fabric extends beyond the silicone rubber and, if of proper mesh, may allow tissue to grow interstitially and further serve to stabilize the implant, the conductors and the shield 21. A small Dacron mesh may be used if it is desired to prevent such interstitial growth. Such extended Dacron fabric 16 structure also provides additional, exposed area for suturing to the body. It may be desirable to fuse or seal the ends of the Dacron or its fibers to prevent their causing irritation within the body.

It may be noted that the Dacron, polyester or other fabric-like material, need not extend beyond the elastomer on three sides, as shown in FIG. 13, but may only extend at one location beyond the elastomer, say, at the end. Alternatively, only a tab of fabric may extend, at one or two sides, of the elastomer. Such tab would still provide a suitable location for suturing to skin or muscle. Such extension of Dacron only at the end of the cover 4, would still allow suturing of the cover and, thus, the implantable device, in place. Of course, the cover is still suturable even if the fabric does not extend beyond the elastomer.

Figure 14:
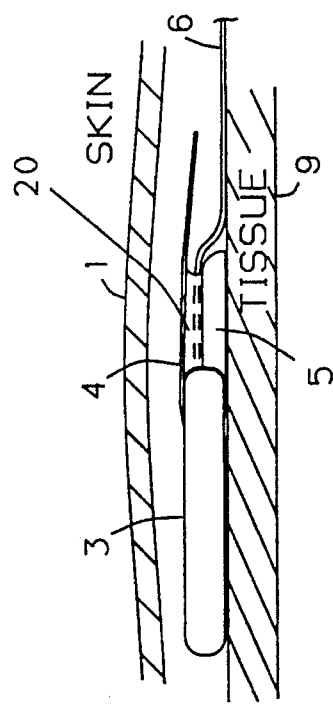
FIG. 14 is a partial cross-section of skin and tissue showing an implanted device, in side view, having the shield attached at one end and a pliant conductor emerging from the shield.

FIG. 14 is a partial cross-section of skin 1 and tissue 9 showings in side view, an implanted device 3 having a bottom shield 9 attached at one end and a pliant conductor 6 emerging from the implantable device 3 and passing through an intermediate body 20. In this embodiment, intermediate body 20 may be constructed in four ways. Intermediate body 20 may be constructed as a third element between cover 4 and bottom shield 5, it may be attached to cover 4, it may be attached to bottom shield 5, or it may integrate or fuse cover 4 and bottom shield 5 into one body. As can be seen, intermediate body 20, together with cover 4 and bottom shield 5, provide strain relief, protection and stability to conductor 6 or to a multiplicity of conductors if such exist. In this embodiment, bottom shield 5 is adapted to lie on tissue or bone or other surface within the body which provides some firmness. Nevertheless, cover 4 may still be sutured to provide additional stabilization and anchoring within the body, so as to prevent movement of the implanted device 3 and conductor 6.

Although specific embodiments and certain structural and electrical arrangements have been illustrated and described herein, it will be clear to those skilled in the art that various other modifications and embodiments may be made incorporating the spirit and scope of the underlying inventive concepts and that the same are not limited to the particular forms herein shown and described except insofar as determined by the scope of the appended claims.

We claim:

1. In combination, an implantable shield, and an implantable device having one or more conductors extending in a particular direction from said device and from a particular location on said device and said one or more conductors being disposed over a particular width at said device, said shield comprising cover means for providing a protective cover for said one or more conductors, means for fixedly mounting said shield to said implantable device, said cover means extending in said direction and from at or near said location, said cover means being at least as wide, at or near said means for fixedly mounting, as said width.

2. The combination of claim 1 wherein said cover means is planar and is comprised of an elastomer.

3. The combination of claim 1 wherein said cover means is suturable to the tissue of a patient and wherein said cover means is adapted to hold a suture for an extended period of time.

4. The combination of claim 3 wherein said suturable, cover means is comprised of a fabric and an elastomer.

5. The combination of claim 1 wherein said cover means is within 3 to 100 thousandths of an inch thick.

6. The combination of claim 1 wherein said cover means is adapted for implantation between one or more of (1) the skin of a patient, (2) the muscle of a patient, and said one or more conductors.

7. The combination of claim 1, wherein said cover means is adapted for implantation adjacent or near a patient's skin.

8. The combination of claim 1, wherein said implantable device is adapted to be implanted between the skin and the skull of a patient and said one or more conductors are adapted to extend from said implantable device along the underside of said skin, and said one or more conductors are adapted to penetrate said skull and wherein said cover means extends to just beyond the location said conductors are adapted to penetrate said skull.

9. The combination of claim 1, wherein said cover means is disposed spaced apart from said location and wherein said cover means is stiffly resilient enough at or near said location so as to resume its original shape after being depressed at said location.

10. The combination of claim 1, wherein said cover means at least partially encircles said one or more conductors for at least a short distance from said means for mounting.

11. The combination of claim 1, wherein said cover means is channel-shaped for partially encircling said one or more conductors.

12. The combination of claim 1, wherein said cover means is L-shaped in profile.

13. The combination of claim 1, wherein said shield is comprised of a bottom portion at least partially encircling and protecting said one or more conductors at or near the location at which said one or more conductors extend from said implantable device.

14. In combination, an implantable shield, and an implantable device having one or more conductors extending in a particular direction from said device and from a particular location on said device, said one or more conductors being disposed over a particular width at said device, said shield comprising cover means for providing protective cover for said one or more conductors, means for fixedly mounting said shield to said implantable device, said cover means having a proximate end and a distal end, said proximate end held in fixed relationship with respect to said means for mounting at or near said means for mounting and said cover means extending along said direction to its distal end, said cover means being at least as wide, at or near its proximate end, as said width and wherein said cover means is fixedly spaced apart, at said proximate end, from said location and wherein said cover means is flexible at its distal end, with respect to said means for fixedly mounting.

15. In combination, a protective, implantable shield, an implantable device, said shield fixedly attached to said implantable device, said implantable device having one or more conductors extending longitudinally in a particular direction from said implantable device and wherein said one or more conductors extend from said implantable device at a particular location, and wherein said shield comprises a flexible cover extending longitudinally along said direction and adapted to provide protection for said one or more conductors against movement, and wherein said shield comprises means for at least partially encircling said one or more conductors at the location at which they extend from said implantable device.

16. The combination of claim 15, wherein said shield comprises a slot extending transversely through said shield except for said cover, said slot being disposed in said shield opposite said cover, and wherein said slot provides a path for said one or more conductors to change direction.

17. The combination of claim 16, wherein said slot is a closed slot.

18. The combination of claim 15, wherein said implantable shield has a recess at one end thereof, receiving said implantable device and wherein said implantable device is adhered to said implantable shield within said recess.

19. The combination of claim 18, wherein said recess is formed between two tapered lips extending from said shield, and wherein said implantable shield is fixedly attached to said implantable device by said lips being adhered to said implantable device and wherein said implantable shield is approximately the same thickness as said implantable device.

20. The combination of claim 18 wherein said means for partially encircling is comprised of a bottom shield wherein said cover and said bottom shield are connected to be a unitary structure and said bottom shield comprises a slot therethrough for receiving said one or more conductors.

21. The combination of claim 15, wherein said shield is of a thickness approximately the same as the thickness of said implantable device.

22. The combination of 15, wherein said implantable device has a plurality of faces, and wherein said cover is substantially planar and is substantially co-planar with one face of said implantable device.

23. The combination of claim 15, wherein said shield is adapted to entirely encircle said one or more conductors by being comprised of a channel through said shield.

24. The combination of claim 23, wherein said channel provides a close fit with said one or more conductors.

25. The combination of claim 24, wherein said channel provides said close fit by converging in a direction away from said location.

26. In combination, an implantable cover and an implantable device having one or more conductors extending therefrom, said cover comprised of a biocompatible elastomer and fixedly mounted at one end with respect to said conductors and said cover being flexible at its other end, said cover disposed to provide protective cover for said one or more conductors against pressure transmitted toward said one or more conductors.

27. The combination recited in claim 26 wherein said cover is adapted to receive and hold a suture for several months or longer.

28. In combination, cover means for providing a protective cover and an implantable device having one or more conductors extending therefrom at a particular location on said device and in a particular direction from said device, said cover means fixedly mounted with respect to said implantable device at or near said location, said cover means disposed so as to extend in said direction and wherein said cover means is further disposed to cover said conductors and protect them against pressure and dislodgment and wherein said cover means comprises at least two planar layers, one, a biocompatible, non-biodegradable fabric and the other, an elastomer.

29. The combination of claim 18, wherein at least a portion of said fabric extends beyond an edge of said elastomer.

30. The combination of claim 18, wherein said cover means comprises one layer of fabric laminated between two layers of elastomer.

31. The combination of claim 30 wherein said fabric at least partially extends beyond edges of said elastomer layers.

* * * * *